United States Patent
Smith

(10) Patent No.: US 8,206,358 B2
(45) Date of Patent: Jun. 26, 2012

(54) RING AND SEAL FOR TROCAR

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 105 days.

(21) Appl. No.: 12/754,983

(22) Filed: Apr. 6, 2010

(65) Prior Publication Data
US 2010/0286617 A1   Nov. 11, 2010

Related U.S. Application Data

(60) Provisional application No. 61/175,924, filed on May 6, 2009.

(51) Int. Cl.
*A61M 5/178* (2006.01)

(52) U.S. Cl. .................................. 604/167.01

(58) Field of Classification Search ............. 604/167.01, 604/167.03, 167.06, 256, 164.01, 164.08, 604/164.11, 165.02, 167.02, 167.04; 606/108, 606/191
See application file for complete search history.

(56) References Cited

U.S. PATENT DOCUMENTS

| | | | |
|---|---|---|---|
| 3,402,710 A | 9/1968 | Paleschuck | |
| 4,447,237 A | 5/1984 | Frisch et al. | |
| 4,475,548 A | 10/1984 | Muto | |
| 4,519,908 A | 5/1985 | Woodruff | |
| 4,553,760 A | 11/1985 | Reed et al. | |
| 4,610,665 A | 9/1986 | Matsumoto et al. | |
| 5,015,228 A | 5/1991 | Columbus et al. | |
| 5,041,095 A | 8/1991 | Littrell | |
| 5,104,389 A | 4/1992 | Deem et al. | |
| 5,127,626 A | 7/1992 | Hilal et al. | |
| 5,180,376 A | 1/1993 | Fischell | |
| 5,207,656 A | 5/1993 | Kranys | |
| 5,330,497 A | 7/1994 | Freitas et al. | |
| 5,338,313 A | 8/1994 | Mollenauer et al. | |
| 5,342,315 A | 8/1994 | Rowe et al. | |
| 5,360,417 A | 11/1994 | Gravener et al. | |
| 5,389,080 A | 2/1995 | Yoon | |
| 5,389,081 A | 2/1995 | Castro | |
| 5,391,153 A | 2/1995 | Haber et al. | |
| 5,407,434 A | 4/1995 | Gross | |

(Continued)

FOREIGN PATENT DOCUMENTS

AU     2005202133 A1     12/2006

(Continued)

OTHER PUBLICATIONS

European Search Report for EP 10 25 0875 date of completion is Aug. 24, 2010 (3 pages).

*Primary Examiner* — Christopher D Koharski

(57) ABSTRACT

A surgical access apparatus for passing through tissue to an underlying surgical area includes an access member defining a longitudinal axis and having a longitudinal channel for reception of a surgical object, a seal member mounted to the access member and positioned to intersect the longitudinal channel, and having internal seal surfaces defining a passage and being dimensioned to establish a substantial sealing relation with a surgical object inserted therethrough and a substantially annular element mounted to the seal member and at least partially circumscribing the passage. The annular member is rigid relative to the seal member and defines an opening to permit passage of the object. The annular element is dimensioned to minimize offset manipulation of the surgical object relative to the longitudinal axis.

12 Claims, 4 Drawing Sheets

U.S. PATENT DOCUMENTS

| | | | |
|---|---|---|---|
| 5,429,609 A | 7/1995 | Yoon | |
| 5,441,486 A | 8/1995 | Yoon | |
| 5,460,616 A | 10/1995 | Weinstein et al. | |
| 5,480,410 A | 1/1996 | Cuschier et al. | |
| 5,484,425 A | 1/1996 | Fischell et al. | |
| 5,514,109 A | 5/1996 | Mollenauer et al. | |
| 5,514,133 A | 5/1996 | Golub et al. | |
| 5,542,931 A | 8/1996 | Gravener et al. | |
| 5,550,363 A | 8/1996 | Obata | |
| 5,556,387 A | 9/1996 | Mollenauer et al. | |
| 5,603,702 A | 2/1997 | Smith et al. | |
| 5,628,732 A | 5/1997 | Anloon, Jr. et al. | |
| 5,634,908 A | 6/1997 | Loomas | |
| 5,634,937 A | 6/1997 | Mollenauer et al. | |
| 5,653,705 A | 8/1997 | de la Torre et al. | |
| 5,662,615 A | 9/1997 | Blake, III | |
| 5,722,958 A | 3/1998 | Gravener et al. | |
| 5,738,664 A | 4/1998 | Erskine et al. | |
| 5,741,298 A | 4/1998 | MacLeod | |
| 5,743,884 A | 4/1998 | Hasson et al. | |
| 5,779,697 A | 7/1998 | Glowa et al. | |
| 5,788,676 A | 8/1998 | Yoon | |
| 5,843,031 A | 12/1998 | Hermann | |
| 5,906,577 A | 5/1999 | Beane et al. | |
| 5,957,913 A | 9/1999 | de la Torre et al. | |
| 5,989,233 A | 11/1999 | Yoon | |
| 6,017,356 A | 1/2000 | Frederick et al. | |
| 6,024,736 A | 2/2000 | de la Torre | |
| 6,079,692 A | 6/2000 | Powell | |
| 6,110,154 A | 8/2000 | Shimomura et al. | |
| 6,123,689 A | 9/2000 | To et al. | |
| 6,315,770 B1 | 11/2001 | de la Torre et al. | |
| 6,319,246 B1 | 11/2001 | de la Torre et al. | |
| 6,355,014 B1 | 3/2002 | Zadno-Azizi et al. | |
| 6,440,063 B1 | 8/2002 | Beans et al. | |
| 6,482,181 B1 | 11/2002 | Racenet et al. | |
| 6,551,283 B1 | 4/2003 | Guo et al. | |
| 6,569,120 B1 | 5/2003 | Green et al. | |
| 6,602,240 B2 | 8/2003 | Hermann et al. | |
| 6,610,031 B1 | 8/2003 | Chin | |
| 6,663,598 B1 | 12/2003 | Carrillo, Jr. et al. | |
| 6,702,787 B2 | 3/2004 | Racenet et al. | |
| 6,712,791 B2 | 3/2004 | Lui et al. | |
| 6,729,624 B1 | 5/2004 | Johnston | |
| 7,052,454 B2 | 5/2006 | Taylor | |
| 7,153,261 B2 | 12/2006 | Wenchell | |
| 7,163,510 B2 | 1/2007 | Kahle et al. | |
| 7,235,062 B2 | 6/2007 | Brustad | |
| 7,244,244 B2 | 7/2007 | Racenet et al. | |
| 7,390,317 B2 | 6/2008 | Taylor et al. | |
| 7,473,221 B2 | 1/2009 | Ewers et al. | |
| 7,481,765 B2 | 1/2009 | Ewers et al. | |
| 2001/0041871 A1 | 11/2001 | Brimhall | |
| 2001/0049499 A1 | 12/2001 | Lui et al. | |
| 2001/0049508 A1 | 12/2001 | Fangrow, Jr. et al. | |
| 2002/0013552 A1 | 1/2002 | Dennis | |
| 2003/0032858 A1 | 2/2003 | Ginn et al. | |
| 2003/0040711 A1 | 2/2003 | Racenet et al. | |
| 2003/0050604 A1 | 3/2003 | Lui et al. | |
| 2003/0139756 A1 | 7/2003 | Brustad | |
| 2003/0195472 A1 | 10/2003 | Green et al. | |
| 2003/0208104 A1 | 11/2003 | Carrillo, Jr. et al. | |
| 2004/0015185 A1 | 1/2004 | Ewers et al. | |
| 2004/0054353 A1 | 3/2004 | Taylor | |
| 2004/0059297 A1 | 3/2004 | Racenet et al. | |
| 2004/0066008 A1 | 4/2004 | Smith | |
| 2004/0093018 A1 | 5/2004 | Johnson | |
| 2004/0106942 A1 | 6/2004 | Taylor et al. | |
| 2004/0111060 A1 | 6/2004 | Racenet et al. | |
| 2004/0162531 A1* | 8/2004 | Wenchell ..................... 604/264 |
| 2004/0254426 A1 | 12/2004 | Wenchell | |
| 2005/0020884 A1 | 1/2005 | Hart et al. | |
| 2005/0059934 A1 | 3/2005 | Wenchell | |
| 2005/0096605 A1 | 5/2005 | Green et al. | |
| 2005/0096695 A1 | 5/2005 | Olich | |
| 2005/0148823 A1 | 7/2005 | Vaugh et al. | |
| 2005/0165433 A1 | 7/2005 | Haberland et al. | |
| 2005/0212221 A1 | 9/2005 | Smith et al. | |
| 2005/0267419 A1 | 12/2005 | Smith | |
| 2006/0041232 A1 | 2/2006 | Steams et al. | |
| 2006/0047284 A1 | 3/2006 | Gresham | |
| 2006/0047293 A1 | 3/2006 | Haberland et al. | |
| 2006/0084842 A1 | 4/2006 | Hart et al. | |
| 2006/0129165 A1 | 6/2006 | Edoga et al. | |
| 2006/0149305 A1 | 7/2006 | Cuevas et al. | |
| 2006/0224120 A1 | 10/2006 | Smith et al. | |
| 2006/0264991 A1 | 11/2006 | Johnson et al. | |
| 2006/0276751 A1 | 12/2006 | Haberland et al. | |
| 2007/0055107 A1 | 3/2007 | Wenchell | |
| 2007/0088241 A1 | 4/2007 | Brustad et al. | |
| 2007/0116854 A1 | 5/2007 | Taylor et al. | |
| 2007/0151566 A1 | 7/2007 | Kahle et al. | |
| 2007/0197972 A1* | 8/2007 | Racenet et al. ........... 604/167.06 |
| 2007/0197992 A1* | 8/2007 | Martynus et al. ........ 604/385.19 |
| 2007/0233006 A1 | 10/2007 | Brustad | |
| 2008/0011307 A1 | 1/2008 | Beckman et al. | |
| 2008/0033363 A1 | 2/2008 | Haberland et al. | |
| 2008/0077169 A1 | 3/2008 | Taylor et al. | |
| 2008/0086074 A1 | 4/2008 | Taylor et al. | |
| 2009/0048683 A1 | 2/2009 | Morris et al. | |
| 2009/0076465 A1 | 3/2009 | Berry et al. | |

FOREIGN PATENT DOCUMENTS

| | | |
|---|---|---|
| DE | 3217118 | 8/1983 |
| DE | 3737121 | 11/1989 |
| EP | 0051718 | 5/1982 |
| EP | 0113520 | 7/1984 |
| EP | 0169787 | 1/1986 |
| EP | 0312219 | 4/1989 |
| EP | 0538060 | 4/1993 |
| EP | 1629787 | 3/2006 |
| EP | 1 698 291 | 6/2008 |
| GB | 1482857 | 8/1977 |
| JP | 50-112652 | 9/1975 |
| JP | 58163867 | 9/1983 |
| JP | 51-03854 | 4/1993 |
| JP | 06061518 | 4/1994 |
| JP | 07241298 | 9/1995 |
| WO | WO 93/04717 | 3/1993 |
| WO | WO 94/17844 | 8/1994 |
| WO | WO 95/13313 | 5/1995 |
| WO | WO 98/53865 | 3/1998 |
| WO | WO 02/087682 | 11/2002 |
| WO | WO 03/011154 | 2/2003 |
| WO | WO 2004/043275 | 5/2004 |
| WO | WO 2007/119232 A | 10/2007 |

* cited by examiner

RING AND SEAL FOR TROCAR

CROSS REFERENCE TO RELATED APPLICATION

The present application claims the benefit of and priority to U.S. Provisional Application Ser. No. 61/175,924 filed on May 6, 2009, the entire contents of which are incorporated herein by reference.

TECHNICAL FIELD

The present disclosure relates to surgical devices and, more particularly, relates to a seal assembly for use with a surgical access device during a minimally invasive surgical procedure, for example, in both laparoscopic and endoscopic procedures.

DESCRIPTION OF ART

Minimally invasive surgical procedures avoid open invasive surgery in favor of closed or local surgery with less trauma. These procedures involve use of laparoscopic devices and remote-control manipulation of instruments with indirect observation of the surgical field through an endoscope or similar device, and are carried out through the skin or through a body cavity or anatomical opening. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith and provides a substantially fluid tight seal about the instrument to preserve the integrity of the established air or gas within the surgical region.

Minimally invasive procedures have several advantages over traditional open surgery, including less patient trauma, reduced recovery time, reduced potential for infection, etc. However, minimally invasive surgery, such as laparoscopy, has several disadvantages. In particular, the frictional forces exerted on surgical instruments inserted through it, has proved to be difficult in procedures requiring extensive manipulation of the long narrow endoscopic instruments within a remote site because of the restricted mobility. In addition, known seal devices are deficient in resilience and in rigidity for affixing the seal within a cannula or trocar housing.

SUMMARY

The present disclosure relates to a surgical access apparatus for passing through tissue to an underlying surgical area. The apparatus includes an access member defining a longitudinal axis and having a longitudinal channel for reception of a surgical object, a seal member mounted to the access member and positioned to intersect the longitudinal channel, and having internal seal surfaces defining a passage and being dimensioned to establish a substantial sealing relation with a surgical object inserted therethrough and a substantially annular element mounted to the seal member and at least partially circumscribing the passage. The annular member is rigid relative to the seal member and defines an opening to permit passage of the object. The annular element is dimensioned to minimize offset manipulation of the surgical object relative to the longitudinal axis.

The annular element may be at least partially embedded within the seal member. The annular element is mounted in a radial outward relation to the internal seal surfaces of the seal member whereby the internal seal surfaces engage the surgical object in substantial sealed relation therewith. The annular element may be substantially planar and arranged in general transverse relation to the longitudinal axis.

The seal member may define a generally tapered configuration. In this embodiment, the seal member may define a proximal seal face and a distal seal face with the proximal seal face at least partially defining the internal seal surfaces. The annular element may be mounted between the proximal seal face and the distal seal face. In the alternative, the seal member may define a substantially planar configuration. The seal member may comprise an elastomeric material and a fabric material.

BRIEF DESCRIPTION OF THE DRAWINGS

Various embodiments of the present disclosure will be described hereinbelow with reference to the figures wherein.

DETAILED DESCRIPTION

The seal assembly of the present disclosure, either alone or in combination with a seal system internal to a cannula assembly, provides a substantial seal between a body cavity of a patient and the outside atmosphere before, during and after insertion of an object through the cannula assembly. Moreover, the seal assembly of the present disclosure is capable of accommodating objects of varying diameters, e.g., instruments from about 4.5 mm to about 15 mm, while maintaining a fluid tight interface about the instrumentation adapted for insertion through a trocar and/or cannula assembly to prevent gas and/or fluid leakage so as to preserve the atmospheric integrity of a surgical procedure. The flexibility of the present seal assembly greatly facilitates endoscopic and/or laparoscopic surgery where a variety of instruments having differing diameters are often needed during a single surgical procedure. Specifically, the surgical device includes a seal assembly which permits and limits some lateral and/or angular manipulation of the surgical instrument while also maintaining a seal about the instrument. The seal assembly is further adapted to substantially close in the absence of a surgical instrument to maintain the integrity of the insufflated peritoneal cavity.

The surgical seal assembly of the present disclosure is additionally adapted to decrease the frictional forces exerted on surgical instruments inserted through it which has proven to be difficult in procedures requiring extensive manipulation of the long narrow endoscopic instruments within a remote site because of the restricted mobility.

Examples of surgical instrumentation include clip appliers, graspers, dissectors, retractors, staplers, laser probes, photographic devices, endoscopes and laparoscopes, tubes, and the like. Such instruments will be collectively referred to herein as "instruments" or "instrumentation".

The seal assembly may also be adapted dimensionally to receive and form a seal about a physician's arm or hand during a hand-assisted laparoscopic procedure. In this application, the seal assembly is a component of an access member which is introduced within the body to provide access to underlying tissue in, e.g., the abdominal cavity.

Moreover, the seal assembly may be readily incorporated into an access device, such as a conventional trocar device or cannula housing to provide the device with zero-closure and/or sealing around an instrument or other object.

In the following discussion, the term "proximal" or "trailing" will refer to the portion of the surgical device nearest to the clinician during operation while the term "distal" or "leading" will refer to that portion of the portal apparatus most remote to the clinician.

Figure 1:
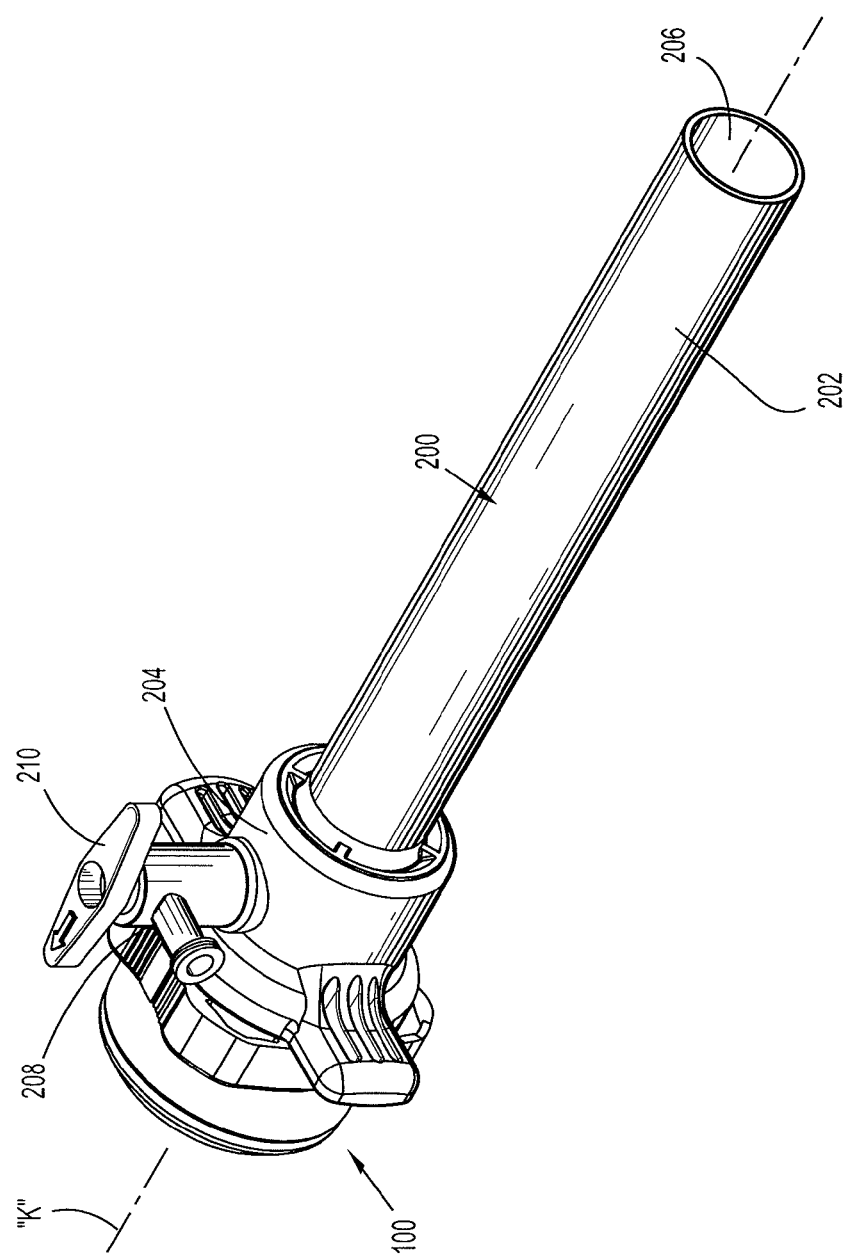
FIG. 1 is a perspective views of an access assembly and a seal assembly in accordance with the principles of the present disclosure.
Figure 2:
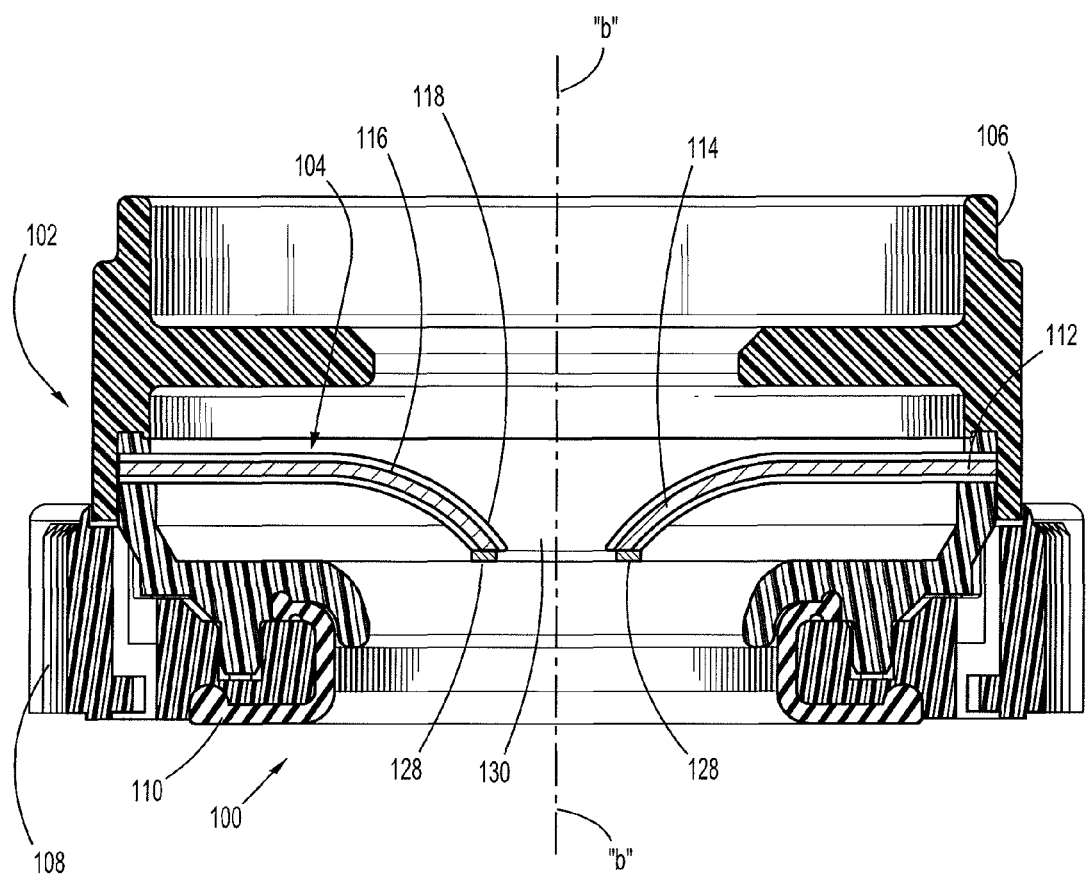
FIG. 2 is a side cross-sectional view of the seal assembly.

Referring now to the drawings, in which like reference numerals identify identical or substantially similar parts throughout the several views, FIGS. 1-2 illustrate one embodiment of a seal assembly, i.e. seal assembly 100 of the present disclosure mounted to an access device such as cannula or trocar assembly 200. Cannula assembly 200 may be any conventional cannula suitable for the intended purpose of accessing a body cavity and typically defines a passageway permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which may be blunt, a non-bladed, or a sharp pointed instrument positionable within the passageway of the cannula assembly 200. The obturator assembly is utilized to penetrate the abdominal wall or introduce the cannula assembly 200 through the abdominal wall, and then subsequently is removed from the access device to permit introduction of the surgical instrumentation utilized to perform the procedure through the passageway. Cannula assembly 200 includes cannula sleeve 202 and cannula housing 204 mounted to an end of the sleeve 202. Any means for mounting cannula sleeve 202 to cannula housing 204 are envisioned including threaded arrangements, bayonet coupling, snap-fit arrangements, adhesives, etc. Cannula sleeve 202 and cannula housing 204 may be integrally formed. Cannula sleeve 202 defines a longitudinal axis "k" extending along the length of sleeve 202. Sleeve 202 further defines an internal longitudinal passage 206 dimensioned to permit passage of surgical instrumentation. Sleeve 202 may be formed of stainless steel or other rigid materials such as a polymeric material or the like. Sleeve 202 may be clear or opaque. The diameter of sleeve 202 may vary, but, typically ranges from about 10 mm to about 15 mm for use with the seal assembly 100 of the present disclosure.

Cannula housing 204 includes luer connector 208. Luer connector 208 is adapted for connection to a supply of insufflation gaseous is conventional in the art and incorporates valve 210 to selectively open and close the passage of the luer connector 208. Cannula housing 204 may further include a duckbill or zero closure valve (not shown) adapted to close upon exposure to the forces exerted by the insufflation gases in the internal cavity. Other zero closure valves are also contemplated including single or multiple slit valve arrangements, trumpet valves, flapper valves, etc.

Figure 3:
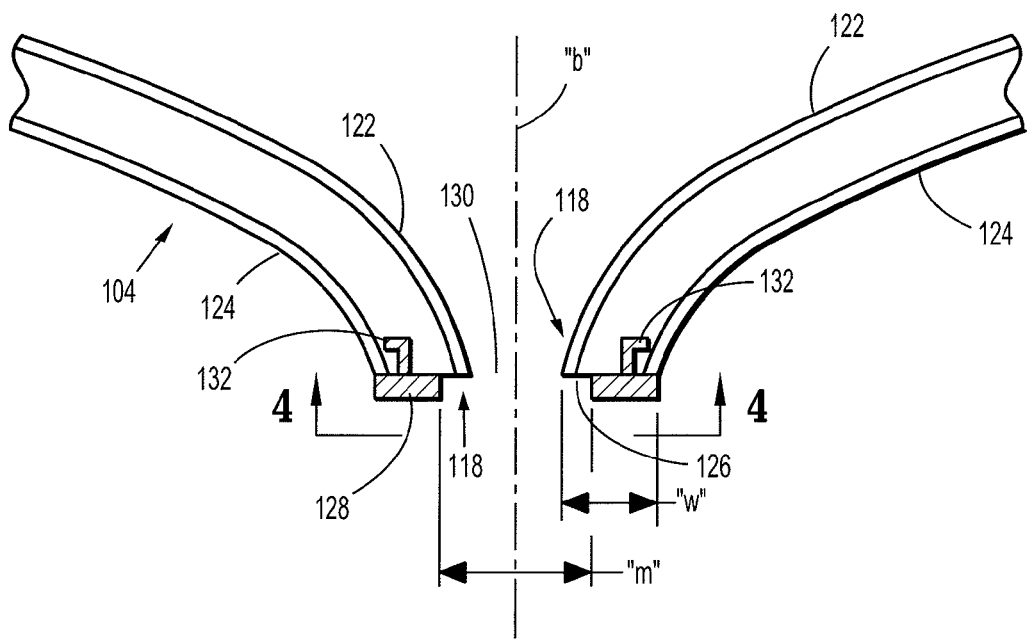
FIG. 3 is an isolated cross-sectional view of the seal member of the seal assembly.

With reference to FIGS. 2-3, seal assembly 100 will be discussed in detail. Seal assembly 100 may be a separate component from cannula assembly 200 and, accordingly, adapted for releasable connection to the cannula assembly 200. Alternatively, seal assembly 100 may be incorporated as part of cannula assembly 200. Seal assembly 100 includes a seal housing, generally identified as reference numeral 102, and seal member 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "k" of cannula sleeve 202 and, more specifically, coincident with the axis "k" of the cannula sleeve 202. Seal housing 102 incorporates three housing components, namely, first, second and third housing components 106, 108, 110, respectively, which, when assembled together, form the seal housing 102. Assembly of housing components 106, 108, 110 may be affected by any of the aforementioned connection means discussed with respect to cannula housing 204.

Seal member 104 may be mounted within seal housing 102 by any conventional means. In one embodiment, seal member 104 includes an outer peripheral segment 112 which is otherwise attached, mounted or connected to seal housing 102. Outer peripheral segment 112 may or may not have an undulation to permit lateral movement of seal member 104 within the seal housing 102. Outer peripheral segment 108 may be secured to seal housing 102 by any conventional means.

Seal member 104 defines a general tapered configuration having a longitudinal component of direction with respect to seal axis "b". Seal member 104 may include an elastomeric material 114 having one or more fabric layers 116 impregnated or mounted to the elastomeric material. A suitable seal 104 is the seal disclosed in commonly assigned U.S. Pat. No. 6,702,787 to Racenet, the entire contents of which are incorporated herein by reference. Fabric layer or material 116 may be, for example, a SPANDEX material containing 20% LYCRA available from Milliken. The elastomeric material may be polyisoprene or a natural rubber. In the embodiment shown in FIG. 2, two fabric layers 116 are arranged to enclose elastomeric material 114. Other arrangements are also envisioned.

Seal member 112 has inner seal surfaces 118 which define a passage 120 for passage of the surgical object. The passage 120 may be normally closed or may be in the form of an aperture which is open in at rest condition. Inner seal surfaces 118 adjacent passage 120 may be elastomeric to facilitate formation of the seal about the inserted object. Seal member 112 defines proximal seal face 122, distal seal face 124 and intermediate seal face 126 disposed between the proximal and distal seal faces 122, 124. Inner seal surfaces 118 establish a seal about the inserted object. Inner seal surfaces 118 may include portions of proximal seal face 122 and intermediate seal face 126.

Seal member 112 has a substantially annular element or ring 128 mounted to or embedded within the seal member 112 adjacent passage 120. Annular element 128 may be formed from any suitable material which is rigid relative to the elastomeric material of inner surfaces 118. Suitable materials include polymeric materials, steel, titanium, etc. Annular element 128 defines an opening 130 for passage of the surgical object. Opening 130 generally defines an internal dimension or diameter which is greater than the diameter of the surgical object or instrument to be positioned within cannula sleeve 202. Annular element 128 may further include anchoring elements 132 depending from the proximal face of the annular element 128. Anchoring elements 132 may be embedded within seal member 112 to secure annular element 128 to the seal member 112. Anchoring elements 132 may be embedded during a molding process utilized in manufacturing seal member 112. In the alternative, annular element 128 may be devoid of anchoring elements 132, and secured to seal member 112 through adhesives, cements, etc.

Figure 4:
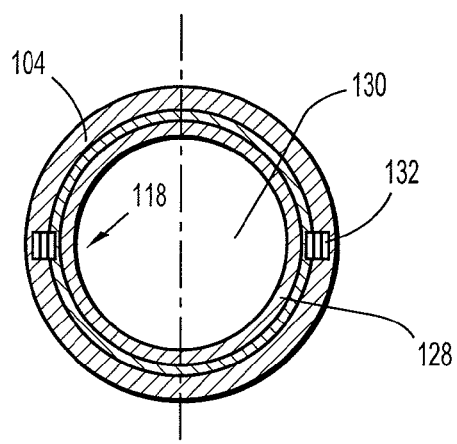
FIG. 4 is a cross-sectional view taken along the lines 4-4 of FIG. 3.

In the embodiment of FIGS. 2-4, annular element 128 is mounted to intermediate end face 126 of seal member 112. The width "w" of annular element 128 may be less than the corresponding width of intermediate end face 126 of seal member 112. With this arrangement, the inserted instrument will contact the seal member 112, e.g., the elastomeric material and/or the fabric material, at inner seal surfaces 112 whereby a seal is formed about the instrument. The instrument or object may move in a lateral direction however, the presence of annular element 128 will ensure that the passage does not open beyond a predetermined inner diameter, e.g., corresponding to the internal dimensions "m" of the annular element 128. This minimizes the potential of "cat-eyeing", which is the establishment of a gap between the object and the seal.

Seal assembly 100, either alone or in combination with a seal unit/seal assembly internal to cannula assembly 200, provides a substantial seal between a body cavity of a patient and the outside atmosphere both during and subsequent to insertion of an instrument through the cannula. In this manner, insufflation gases are prevented from escaping through the trocar assembly to the outside environment. Seal assembly 100 is preferably detachably mountable to cannula housing 204. Thus, the surgeon can remove the seal assembly 100 from the cannula assembly 200 at any time during the surgical procedure and, similarly, mount the seal assembly 100 to the cannula when desired in order to provide a sealing engagement with an instrument to be inserted through the cannula. In addition, seal assembly 100 may be readily adapted for mounting to conventional cannulas of differing structures. The detachability of seal assembly 100 from cannula assembly 200 facilitates specimen removal through cannula assembly 200.

Figure 5:
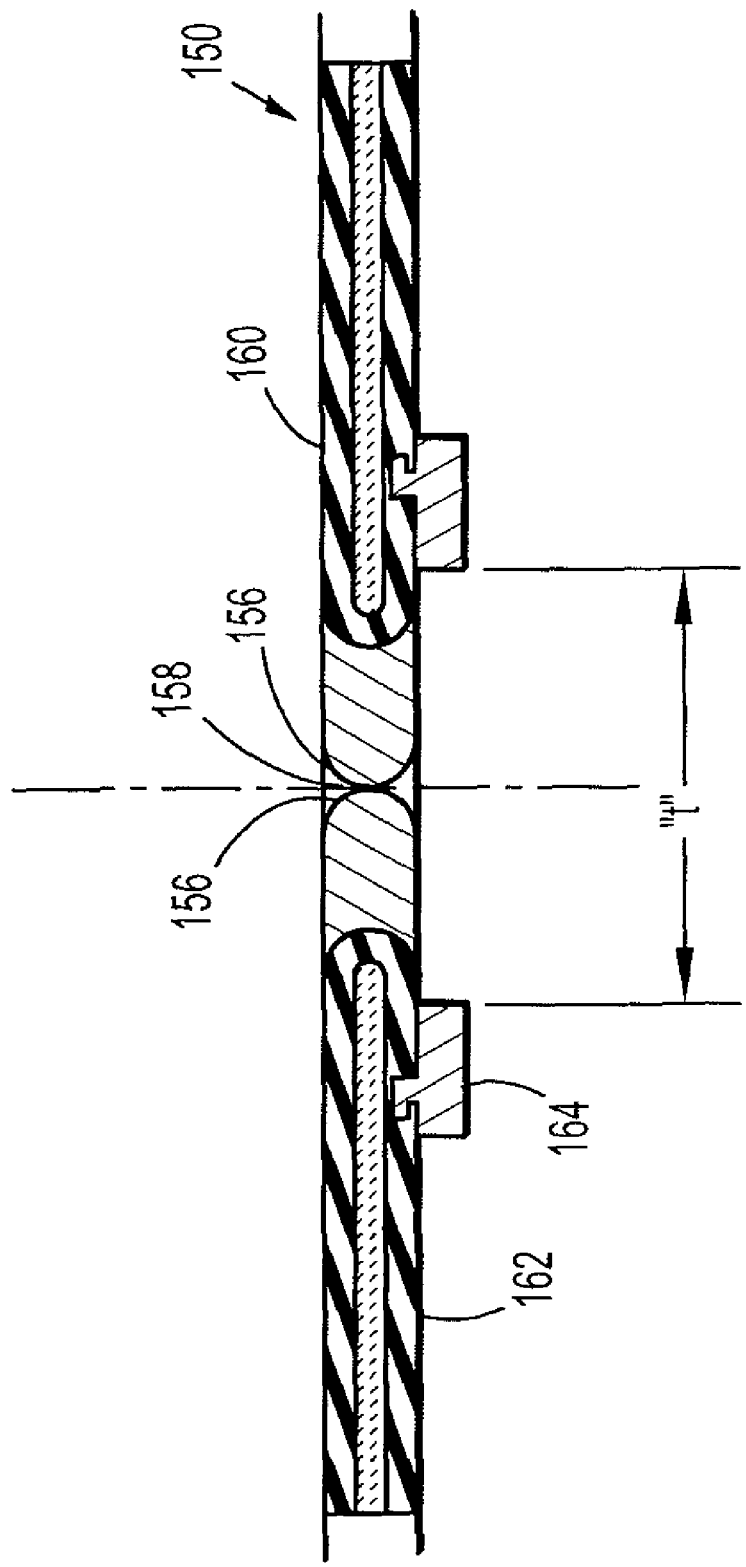
FIG. 5 is a side cross-sectional view of an alternate embodiment of the seal member of the seal assembly.

Referring to FIG. 5, an alternate embodiment of seal member 150 for use with the seal assembly 100 is illustrated. Seal member 150 is substantially similar to seal member 104 of the embodiment of FIGS. 1-4. Seal member 150 includes inner planar seal segment 152 and outer segment 154. Inner planar segment 152 has inner seal surfaces 156 defining slit 158 for reception of an object whereby the inner seal surfaces 156 establish a seal about the object. Slit 158 may open for reception of the object and may close in the absence of the object. Thus, seal member 150 also may function as a zero closure valve for maintaining the integrity of the underlying insufflated body cavity. Seal member 150 may, in the alternative, have an aperture in lieu of slit 158. Inner planar segment 152 has proximal and distal faces 160, 162.

Seal member 150 further includes annular element 164 mounted to distal face 162. Annular element 164 may be substantially similar to the annular element 128 discussed hereinabove in connection with the embodiment of FIGS. 1-4. Annular element 164 defines an internal dimension "t" greater than an internal dimension of slit 158. Annular element 164 restricts lateral movement of the surgical object thereby assisting in maintaining the integrity of the seal about the object by, e.g., minimizing "cat-eyeing". In addition, in the event the object is moved laterally or in a radial direction, the forces associated with this movement are transferred to the outer peripheral segment of seal member 150. This may preserve the integrity of inner seal surfaces 156 defining slit 158.

It will be understood that various modifications may be made to the embodiments shown herein. Therefore, the above description should not be construed as limiting, but merely as exemplifications of preferred embodiments. Those skilled in the art will envision other modifications within the scope and spirit of the presently disclosed seal assemblies.

What is claimed is:

1. A surgical access apparatus for passing through tissue to an underlying surgical area, which comprises:
    an access member defining a longitudinal axis and having a longitudinal channel for reception of a surgical object;
    a seal member mounted to the access member and positioned to intersect the longitudinal channel, the seal member having internal seal surfaces defining a passage and being dimensioned to establish a substantial sealing relation with a surgical object inserted therethrough; and
    a substantially annular element mounted to the seal member and at least partially circumscribing the passage, the annular member being rigid relative to the seal member and defining an opening to permit passage of the object, the annular element being dimensioned to minimize offset manipulation of the surgical object relative to the longitudinal axis, wherein the seal member defines a proximal seal face, a distal seal face, and an intermediate seal face disposed between the proximal seal face and the distal seal face, wherein the annular element is in contact with the intermediate seal face, and wherein a transverse cross-sectional width of the intermediate seal face is larger than a transverse cross-sectional width of the annular element that is in contact therewith.

2. The surgical access apparatus according to claim 1 wherein the annular element is at least partially embedded within the seal member.

3. The surgical access apparatus according to claim 1 wherein the annular element is mounted in a radial outward relation to the internal seal surfaces of the seal member whereby the internal seal surfaces engage the surgical object in substantial sealed relation therewith.

4. The surgical access apparatus according to claim 3 wherein the seal member defines a generally tapered configuration.

5. The surgical access apparatus according to claim 1, wherein the seal member defines a proximal seal face and a distal seal face, the proximal seal face at least partially defining the internal seal surfaces.

6. The surgical access apparatus according to claim 5, wherein the annular element is substantially planar and is arranged in general transverse relation to the longitudinal axis.

7. The surgical access apparatus according to claim 6, wherein the annular element is mounted between the proximal seal face and the distal seal face.

8. The surgical access apparatus according to claim 3 wherein the seal member defines a substantially planar configuration.

9. The surgical access apparatus according to claim 3 wherein the seal member comprises an elastomeric material and a fabric material.

10. The surgical access apparatus according to claim 1 wherein the annular element is mounted in a radial outward relation to the internal seal surfaces of the seal member such that the annular element does not contact a surgical object when a surgical object is in contact with the seal member.

11. The surgical access apparatus according to claim 1 wherein a proximal seal face of the seal member is free from contact with the annular element.

12. The surgical access apparatus according to claim 3 wherein the seal member is biased in a tapered configuration prior to being contacted by a surgical instrument such that a proximal face of the seal member includes only one of a concave and a convex surface.

* * * * *